United States Patent [19]

McAlpine et al.

[11] 4,418,193
[45] Nov. 29, 1983

[54] METHOD OF PRODUCING 2-EPI-FORTIMICIN A

[75] Inventors: James B. McAlpine, Libertyville; Ronald E. Carney, Gurnee, both of Ill.

[73] Assignee: Abbott Laboratories, North Chicago, Ill.

[21] Appl. No.: 366,800

[22] Filed: Apr. 9, 1982

[51] Int. Cl.³ .............................................. C07H 15/22
[52] U.S. Cl. ................................................... 536/16.1
[58] Field of Search ....................................... 536/16.1

[56] References Cited

U.S. PATENT DOCUMENTS

| | | | |
|---|---|---|---|
| 4,207,415 | 6/1980 | Carney et al. | 536/16.1 |
| 4,272,626 | 6/1981 | Carney et al. | 536/16.1 |
| 4,273,924 | 6/1981 | Martin et al. | 536/16.1 |
| 4,331,804 | 5/1982 | Tadanier et al. | 536/16.1 |

Primary Examiner—Johnnie R. Brown
Attorney, Agent, or Firm—Dennis K. Shelton

[57] ABSTRACT

An improved method of producing 2-epi-fortimicin A directly from fortimicin A by protecting the amine functions of fortimicin A, converting the N-protected fortimicin A to an intermediate of the formula:

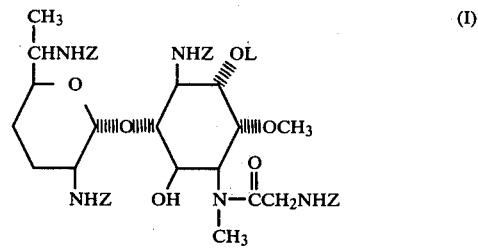

wherein L is a leaving group and Z is an amine-protecting group, reacting the intermediate (I) with a loweralkyl metal halide in N,N-dimethylformamide to form N-protected-2-epi-fortimicin A, and then hydrogenating the N-protected-2-epi-fortimicin A to obtain 2-epi-fortimicin A.

12 Claims, No Drawings

METHOD OF PRODUCING 2-EPI-FORTIMICIN A

BACKGROUND AND SUMMARY OF THE INVENTION

This invention relates to an improved process for producing 2-epi-fortimicin A directly from fortimicin A.

2-epi-fortimicin A is an aminoglycoside antibiotic disclosed in commonly assigned U.S. patent application Ser. No. 79,130, filed September 26, 1979, now U.S. Pat. No. 4,331,804. This compound can be represented by the following structural formula:

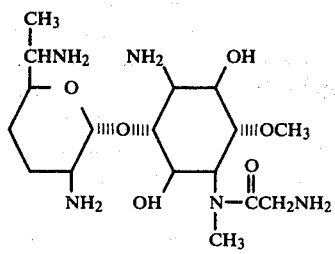
(II)

Prior to the present invention, 2-epi-fortimicin A was obtained by a long and tortuous process through the selective epimerization of fortimicin B at the 2-position and the subsequent conversion of 2-epi-fortimicin B to 2-epi-fortimicin A.

Generally, in order to selectively epimerize the 2-position of fortimicin B, it was necessary to first prepare 1,2′,6′-tri-N-benzyloxycarbonylfortimicin B-4,5-carbamate which was then converted to the 2-O-methanesulfonate intermediate. Solvolysis of the 2-O-methanesulfonate intermediate in the presence of ammonium acetate resulted in an approximately equimolar mixture of the tri-N-benzyloxycarbonyl-2-epi-4,5-carbamate an the 2′,6′-di-N-benzyloxycarbonyl-2-epi biscarbamate. Alternatively, solvolysis of the 2-O-methanesulfonate intermediate in a mixture of tetrahydrofuran and sodium bicarbonate resulted in the 2-epi-oxazoline intermediate. Heating of the latter intermediates under reflux in a solution prepared from ammonium acetate and an aqueous 1,2-dimethoxyethane resulted in an approximately equimolar mixture of the 2-epi-4,5-carbamate intermediate and the 2-epi-biscarbamate intermediate.

The mixture of the 2-epi-mono and biscarbamates were then separated into pure components by chromatography or heated under reflux with a mixture of sodium bicarbonate and methanol to convert the monocarbamate to the biscarbamate which is then isolated by chromatography.

Hydrogenolysis of the 1,2′-di-N-benzyloxycarbonyl-2-epi-biscarbamate with 5% palladium on carbon in the presence of methanolic hydrochloric acid resulted in 2-epi-fortimicin B dihydrochloride. Incomplete hydrolysis results in a mixture of 2-epi-1,4-urea and the desired 2-epi-fortimicin B and care had to be taken to employ a sufficiently long hydrolysis time.

2-epi-Fortimicin B was then converted to 1,2′,6′-tri-N-fortimicin B with N-benzyloxycarbonylsuccinimide. 4-N-acylation of the N-protected intermediate with the N-hydroxysuccinimide ester of N-benzyloxycarbonylglycine resulted in tetra-N-benzyloxycarbonyl-2-O-[N-benzyloxycarbonylglycyl]-2-epi-fortimicin A as the major product and the desired tetra-N-benzyloxycarbonyl-2-epi-fortimicin A is the minor product. Catalytic hydrogenations of the latter compounds with 5% palladium on carbon in 0.2 N-methanolic hydrochloric acid resulted in 2-O-glycyl-2-epi-fortimicin A and 2-epi-fortimicin A, respectively.

Since 2-epi-fortimicin A was obtained as the minor product in the above prior art synthesis, an alternate method of preparing the compound was sought. In that method, fortimicin B was converted to tetra-N-acetyl-fortimicin B and selectively hydrolyzed to provide 1,2′,6′-tri-N-acetylfortimicin B. The latter was converted to the 4-N-ethoxycarbonyl derivative which was then cyclized to the 4,5-carbamate in a refluxing suspension of sodium bicarbonate in aqueous methanol. Treatment of the latter with methanesulfonic acid in pyridine resulted in the 2-epi-1,2-oxazolidine intermediate. Hydrolysis with aqueous hydrochloric acid in tetrahydrofuran resulted in 1,2′,6′-tri-N-acetyl-2-epi-fortimicin B-4,5-carbamate. The latter was then converted to the corresponding 2-O-benzyl ether with benzylbromide in N,N-dimethylformamide in the presence of barium oxide and barium hydroxide. Hydrolysis with aqueous sodium hydroxide resulted in 2-O-benzyl-2-epi-fortimicin B. The latter was then treated with N-benzyloxycarbonylsuccinimide to provide 1,2′,6′-tri-N-benzyloxycarbonyl-2-epi-fortimicin B. Treatment of the latter with the N-hydroxysuccinimide ester of N-benzyloxycarbonylglycine resulted in the tetra-N-benzyloxycarbonyl-2-O-benzyl-2-epi-fortimicin A intermediate. Catalytic hydrogenolysis of the latter in the presence of 5% palladium on carbon finally resulted in the desired product.

In contrast to the foregoing relatively long and arduous methods of obtaining 2-epi-fortimicin A through 2-epi-fortimicin B, the present invention provides a much simplified process of obtaining 2-epi-fortimicin A directly from fortimicin A by protecting the amine groups of fortimicin A, converting the N-protected fortimicin A to an intermediate of the formula:

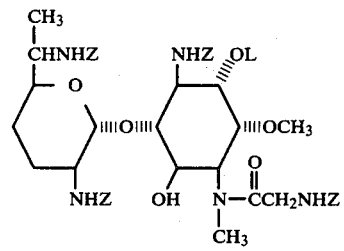
(I)

wherein L is a leaving group and Z is an amine-protecting group, reacting the intermediate (I) with a loweralkyl metal halide in N,N-dimethylformamide to form N-protected-2-epi-fortimicin A, and then removing the N-protecting groups to obtain 2-epi-fortimicin A.

DETAILED DESCRIPTION OF PREFERRED EMBODIMENTS

Suitable protection of the amine groups of fortimicin A is well known in the art. Useful amine-protecting groups include, for example, arylalkoxycarbonyl, alkoxycarbonyl, sulfonyl and acyl amine-protecting groups. Illustrative examples of suitable amine-protecting groups include, for example, benzyloxycarbonyl, triphenylmethyl (trityl), tert-butyloxycarbonyl, p-toluenesulfonyl (tosyl), formyl, acetyl, phthaloyl, and the like. See, for example, Boissonnas, R. A., "Selectively Removable Amino Protective Groups Used in the Synthesis of Peptides", *Advances in Organic Chemistry*, Vol. 3, pp. 159–190 (1963).

The presently most particularly preferred amine-protecting group is benzyloxycarbonyl. In general, the free base of fortimicin A may be dissolved, such as in water and methanol, and treated with the benzyloxycarbonyl ester of N-hydroxy-succinimide, for example, to obtain N-protected fortimicin A.

The N-protected fortimicin A is converted to an intermediate of the formula

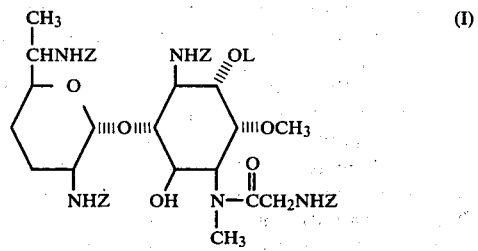

wherein L is a leaving group and Z is an amine protecting group. Suitable leaving groups include any group which will leave the intermediate (I) upon subsequent reaction with an alkyl metal halide and N,N-dimethylformamide. Presently preferred leaving groups for use in connection with the practice of the invention include, for example, sulfonyl groups of the formula —SO$_2$X, wherein X is a straight, branched or cyclic saturated or unsaturated, optionally substituted hydrocarbon moiety having from 1 to 8 carbon atoms, e.g., methanesulfonyl (mesyl), trifluoromethanesulfonyl (triflyl), ethanesulfonyl, benzenesulfonyl, toluenesulfonyl (tosyl), bromotoluenesulfonyl (brosyl), and the like, and thiocarbonyl groups of the formula

wherein Y is imidazolyl. Presently particularly preferred leaving groups are trifluoromethanesulfonyl (triflyl) and thiocarbonylimidazolyl. When the leaving group is thiocarbonylimidazolyl, the intermediate (I) is formed by reacting the N-protected fortimicin A with N,N'-thiocarbonyldiimidazole in a suitable solvent for both, such as ethyl acetate. Although precise proportions of reactants are not critical, the N,N'-thiocarbonyldiimidazole is preferably provided to excess. Completion of the reaction is facilitated by heating the reaction mixture, such as, for example, up to about the reflux temperature of the solvent employed, for about 1 to about 20 hours, more preferably about 2 to about 15 hours, and most preferably about 5 to about 10 hours. When the leaving group is trifluoromethanesulfonyl, the intermediate (I) is formed by reacting the N-protected fortimicin A with trifluoromethanesulfonyl chloride in a suitable solvent, such as pyridine. The reaction may be conducted at room temperature and will typically run to completion in less than about 16 hours.

The intermediate (I) is reacted with a loweralkyl metal halide in N,N-dimethylformamide to form N-protected-2-epi-fortimicin A. As used herein, the term "loweralkyl" means straight or branched chain alkyl groups containing from 1 to 6 carbon atoms, inclusive, and including, but not limited to methyl, ethyl, n-propyl, iso-propyl, n-butyl, sec-butyl, tert-butyl, n-pentyl, 2,3-dimethylpropyl, n-hexyl, 3-methylpentyl, 1,2-dimethylbutyl, etc. Suitable metals include zirconium, germanium, palladium, platinum and tin. The term "halide" means chloride, fluoride, bromide and iodide. Thus, as used herein, the term "loweralkyl metal halide" specifically includes, for example, such alkylmetal halides as triethyl germanium chloride, tri-n-butyl tin chloride, tri-n-propyl tin fluoride, tri-n-butyl tin fluoride, tri-n-butyl tin bromide, and the like, although the presently most particularly preferred loweralkyl metal halide is tri-n-butyl tin fluoride. The reaction of the intermediate (I) with a loweralkyl metal halide is carried out in N,N-dimethylformamide, which appears to play a role in the reaction, and completion of the reaction is facilitated by conducting the reaction at an elevated temperature level, such as up to about the reflux temperature of the solvent, for from about 10 minutes to about 10 hours, more preferably from about 20 minutes to about 5 hours, most preferably from about 30 minutes to about 2 hours.

The N-protected-2-epi-fortimicin A produced in accordance with the foregoing is finally deprotected by techniques well known in the art. Suitable techniques for N-deprotection include catalytic hydrogenolysis, although other techniques may be employed for this purpose. When the amino protecting group is benzyloxycarbonyl, removal of the N-protecting groups is accomplished by subjecting the N-protected-2-epi-fortimicin A to hydrogen, preferably at an elevated pressure level such as, for example, 3 atmospheres, in the presence of a metal catalyst, whereby the N-protecting group is eliminated. Hydrogenolysis may be conducted in a suitable solvent, such as methanol, tetrahydrofuran, dioxane, water, mixtures thereof, and the like. The presently preferred catalyst is palladium on carbon. In addition, the hydrogenolysis may be conducted in the presence of a suitable acid, such as hydrochloric acid, sulfuric acid, and the like to obtain a salt of 2-epi-fortimicin A as the final product. For example, when hydrogenolysis is conducted in the presence of hydrochloric acid, the end product is 2-epi-fortimicin A tetrahydrochloride.

The following examples further illustrate the present invention.

EXAMPLE 1

Tetra-N-benzyloxycarbonylfortimicin A

Fortimicin A sulfate (2.5 g.) was dissolved in water (20 ml) and applied to a column of Dowex 1X2(OH—) resin (Dow Chemical) (1.7×15 cm.). The basic percolate was collected and lyophilized to give 1.51 g. of the free base of fortimicin A. The free base, fortimicin A (1.51 g., 3.74 mmole) was dissolved in a mixture of water (19 ml) and methanol (30 ml), the solution was cooled in an ice bath with stirring and treated with the benzloxycarbonyl ester of N-hydroxysuccinimide (3.8 g., 15.2 mmole). The mixture was allowed to stand at room temperature overnight. Solvent was removed and the crude residue was chromatographed over silica gel to afford 2.25 g. of tetra-N-benzyloxycarbonylfortimicin A.

EXAMPLE 2

Tetra-N-benzyloxycarbonylfortimicin A-2-O-thiocarbonylimidazolide

Tetra-n-benzyloxycarbonylfortimicin A (2.5 g., 2.65 mmole) and N,N'-thiocarbonyldiimidazole (1.0 g., 5.6 mmole) were dissolved in ethylacetate (40 ml) and heated under reflux for 7½ hours. Solvent was removed and the residue chromatographed over silica gel in ethylacetate-isooctane (7:3 v/v) to give 1.9 g. of tetra-N-benzyloxycarbonylfortimicin A-2-O-thiocarbonylimidazolide.

EXAMPLE 3

Tetra-N-benzyloxycarbonyl-2-epi-fortimicin A

To a solution of tetra-N-benzyloxycarbonylfortimicin A-2-O-thiocarbonylimidazolide (1.0 g.) in N,N-dimethylformamide (10 ml) is added tri-n-butyl tin fluoride (280 mg) and the mixture is heated under reflux for one hour. The reaction is cooled to room temperature and evaporated to dryness under reduced pressure. Chromatography of the residue on a column of silica gel eluted with toluene/iso-propyl alcohol [24:1 (v/v)] gives tetra-N-benzyloxycarbonyl-2-epi-fortimicin A. PMR (CDCl$_3$): C'-CH$_3$, 1,14(d), J=6.1 Hz; N-CH$_3$, 2.87; OCH$_3$, 3.48.

EXAMPLE 4

Tetra-N-benzyloxycarbonyl fortimicin A 2-O-triflate

Tetra-N-benzyloxycarbonylfortimicin A (1.0 g.) was dissolved in anhydrous pyridine (20 ml.) and treated with trifluoromethanesulfonyl chloride (0.4 ml.) at room temperature overnight. Solvent was removed and the residue chromatographed over a 1.5 cm×60 cm column of silica gel eluted with ethylacetate to obtain tetra-N-benzyloxycarbonylfortimicin A-2-O-triflate.

IR(7% CDCl$_3$SOl.): 1050, 1220, 1510, 1720 cm$^{-1}$.

| C-1' | 97.3 | C-1 | 53.8 | OCH$_3$ | 57.9 |
|---|---|---|---|---|---|
| C-2' | 49.7 | C-2 | 79.9 | NCH$_3$ | 35.7 |
| C-3' | 23.8 | C-3 | 71.4 | gNCH$_2$ | 43.4 |
| C-4' | 37.4 | C-4 | 57.5 | gNCO | 171.9 |
| C-5' | 71.6 | C-5 | 72.8 | | |
| C-6' | 49.4 | C-6 | 74.2 | | |
| b'CH$_3$ | 18.4 | | | | |

PMR (CDCl$_3$): C' CH$_3$, 1.22(d), J=6.9 Hz; NCH, 2.75; OCH$_3$, 3.31.

EXAMPLE 5

Tetra-N-benzyloxycarbonyl-2-epi-fortimicin A (Alternate Process)

To a solution of tetra-N-benzyloxycarbonylfortimicin A-2-triflate in N,N-dimethylformamide (10 ml) are added an excess of tri-n-butyl tin fluoride and the mixture is heated at reflux for 30 minutes. The reaction is cooled to room temperature and evaporated to a residue under reduced pressure. High pressure liquid chromatographic analysis of the crude product on a M-bond-pack C-18 analytical column eluted with methyl cyanide-water (50:50, v/v) gives a major product with a retention volume identical to that of the tetra-N-benzyloxycarbonyl-2-epi-fortimicin A prepared in Example 3 in a 65 to 70% yield.

EXAMPLE 6

2-Epi-fortimicin A tetrahydrochloride

A solution of tetra-N-benzyloxycarbonyl-2-epi-fortimicin A (134 mg.) in methanolic hydrogen chloride (1.14 ml/0.2 N) is hydrogenated over 5% Pd/C (134 mg.) at three atmospheres of pressure for four hours. The catalyst is removed by filtration and the filtrate evaporated to a residue under reduced pressure to give 2-epi-fortimicin A as the tetrahydrochloride salt (85 mg.). IR(KBr pellet); 1030, 1105, 1480, 1630 cm$^{-1}$; PMR (D$_2$O); C'-CH$_3$, 1.36(d), J=6.8 Hz; N-CH$_3$, 3.19, OCH$_3$, 3.62; MS, found for C$_{17}$H$_{35}$N$_5$P$_6$M/E 405.

As can be seen from the above examples, the multistep process previously required to produce 2-epi-fortimicin A has been replaced by a greatly simplified, economically feasible process.

EXAMPLE 7

1,2',6'-Tri-N-benzyloxycarbonylfortimicin A-2-epi-cis-1,2-carbamate

A second component present in the products formed by the method of Example 3 is observed by thin layer chromatography and high pressure liquid chromatographic analysis, respectively. During a repeat of Example 3 with prolonged heating (approximately 3 hours), the tetra-N-benzyloxycarbonyl-2-epi-fortimicin A disappeared, giving rise to an unidentified major product. The reaction mixture is cooled to room temperature and the solvent removed under reduced pressure. Silica gel chromatography of the residue on a column eluted with toluene-isopropyl alcohol [24:1 (v/v)] gives 1,2',6'-tri-N-benzyloxycarbonylfortimicin A-2-epi-cis-1,2-carbamate. PMR (CDCl$_3$): C'-CH$_3$, 1.13(d), J=6.5 Hz; N-CH$_3$, 2.39; OCH$_3$, 2.95.

EXAMPLE 8

2-epi-Fortimicin A-cis-1,2-carbamate trihydrochloride

A solution of 1,2',6'-tri-N-benzyloxycarbonylfortimicin A-2-epi-cis-1,2-carbamate (212 mg.) in methanolic hydrogen chloride (18 ml/0.2 N) is hydrogenolyzed over 5% Pd/C (210 mg.) at three atmospheres pressure for four hours. The catalyst is removed by filtration and the filtrate evaporated to a residue under reduced pressure to give 2-epi-fortimicin A-cis-1,2-carbamate as the trihydrochloride salt (130 mg.). IR(KBr pellet): 1030, 1105, 1400, 1490, 1640, 1735 cm$^{-1}$. PMR(D$_2$O): C'-CH$_3$, 1.34(d), J=6.9 Hz; N-CH$_3$, 3.09; OCH$_3$, 3.59.

The carbon magnetic resonance spectra of the compounds of Examples 3, 6, 7 and 8 were recorded deuteriochloroform. Only signals assigned to carbons of the fortimicin A skeleton are shown, and these are described in ppm downfield from tetramethylsilane as shown in Table I:

TABLE I

| | CMR Data | | | |
|---|---|---|---|---|
| | Examples | | | |
| | 3 | 6 | 7 | 8 |
| C-1' | 97.9 | 95.3 | 98.7 | 94.1 |
| C-2' | 49.8 | 51.6 | 50.1 | 51.6 |
| C-3' | 24.3 | 21.5 | 24.1 | 21.6 |
| C-4' | 26.9 | 26.3 | 26.5 | 26.3 |
| C-5' | 71.6 | 70.9 | 71.7 | 70.5 |
| C-6' | 49.8 | 49.4 | 50.1 | 49.4 |
| C-CH$_3$ | 17.9 | 15.3 | 17.6 | 15.4 |
| C-1 | 55.6 | 54.7 | 54.1 | 53.7 |
| C-2 | 67.2 | 69.7 | 71.2 | 70.8 |

TABLE I-continued

| | CMR Data Examples | | | |
|---|---|---|---|---|
| | 3 | 6 | 7 | 8 |
| C-3 | 75.7 | 75.2 | 81.5 | 82.2 |
| C-4 | 55.6 | 55.7 | 56.1 | 56.0 |
| C-5 | 72.8 | 70.9 | 74.6 | |
| C-6 | 73.5 | 73.1 | 75.4 | 75.7 |
| OCH$_3$ | 59.3 | 59.8 | 58.3 | 58.9 |
| NCH$_3$ | 35.4 | 32.4 | 32.2 | 32.3 |
| GlyCH$_2$ | 43.4 | 41.3 | 43.1 | 41.3 |
| GlyCO | 170.5 | 168.9 | 170.0 | 169.0 |

What is claimed is:

1. An improved method of producing 2-epi-fortimicin A, comprising (a) converting an N-protected fortimicin A compound to an intermediate (I) of the formula:

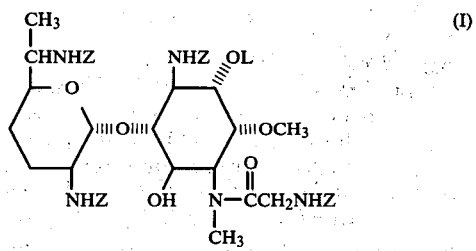

wherein L is a leaving group and Z is an amine protecting group; (b) reacting the intermediate (I) with a loweralkyl metal halide in the presence of N,N-dimethylformamide to produce N-protected-2-epi-fortimicin A; and (c) subjecting the N-protected-2-epi-fortimicin A to catalytic hydrogenolysis to obtain 2-epi-fortimicin A.

2. The method of claim 1 wherein L is sulfonyl of the formula —SO$_2$X, wherein X is a straight, branched or cyclic hydrocarbon moiety having from 1 to 8 carbon atoms.

3. The method of claim 2 wherein X is methyl, trifluoromethyl, ethyl, benzyl, tolyl, or bromotolyl.

4. The method of claim 3 wherein L is trifluoromethanesulfonyl.

5. The method of claim 4 wherein tetra-N-benzyloxycarbonylfortimicin A is reacted with trifluoromethanesulfonyl chloride to obtain tetra-N-benzyloxycarbonylfortimicin A 2-O-triflate.

6. The method of claim 1 wherein L is thiocarbonylimidazoyl.

7. The method of claim 6 wherein tetra-N-benzyloxycarbonylfortimicin A is reacted with N,N'-thiocarbonyldiimidazole to obtain tetra-N-benzyloxycarbonylfortimicin A 2-O-thiocarbonylimidazolide.

8. The method of claims 1, 2 3, 4, 5, 6 or 7 wherein the loweralkyl metal halide is tri-n-butyl tin fluoride.

9. The method of claim 8 wherein the intermediate is refluxed in the presence of tri-n-butyl tin fluoride to obtain N protected 2-epi-fortimicin A.

10. The method of claim 1 wherein the primary amino groups of fortimicin A are protected by reacting fortimicin A with the benzyloxycarbonyl ester of N-hydroxysuccinimide to obtain tetra-N-benzyloxycarbonylfortimicin A.

11. The method of claim 10 wherein the tetra-N-benzyloxycarbonyl-2-epi-fortimicin A is subjected to hydrogenolysis over palladium on carbon catalyst in the presence of hydrogen to obtain 2-epi-fortimicin A.

12. The method of claim 11 wherein the tetra-N-benzyloxycarbonyl-2-epi-fortimicin A is dissolved in hydrochloric acid prior to hydrogenolysis to obtain the tetrahydrochloride salt of 2-epi-fortimicin A after said hydrogenolysis.

* * * * *